(12) United States Patent
Duncan et al.

(10) Patent No.: US 7,411,049 B2
(45) Date of Patent: Aug. 12, 2008

(54) HYBRIDOMA CELL LINES AND MONOCLONAL ANTIBODIES RECOGNIZING PROX1

(75) Inventors: Melinda K. Duncan, Elkton, MD (US); Xiaoren Chen, Newark, DE (US); William Cain, Newark, DE (US)

(73) Assignee: University of Delaware, Newark, DE (US)

( * ) Notice: Subject to any disclaimer, the term of this patent is extended or adjusted under 35 U.S.C. 154(b) by 0 days.

(21) Appl. No.: 11/502,901

(22) Filed: Aug. 11, 2006

(65) Prior Publication Data

US 2007/0048313 A1    Mar. 1, 2007

Related U.S. Application Data

(60) Provisional application No. 60/710,921, filed on Aug. 24, 2005.

(51) Int. Cl.
*C07K 16/00* (2006.01)
*C07K 16/26* (2006.01)
*C12N 5/06* (2006.01)

(52) U.S. Cl. ............ 530/388.1; 530/388.2; 530/388.23; 530/388.24; 435/326

(58) Field of Classification Search ........................ None
See application file for complete search history.

(56) References Cited

U.S. PATENT DOCUMENTS 5,055,405 A    10/1991    Wang et al.
6,818,215 B2   11/2004    Smith et al.

OTHER PUBLICATIONS

J.T. Wigle et al., "Prox1 function is crucial for mouse lens-fibre elongation," *Nature Genetics*, (Mar. 1999), pp. 318-322, vol. 21.
M.K. Duncan et al., "Prox1 is differentially localized during lens development," *Mechanisms of Development*, (2002), pp. 195-198, vol. 112.
Kohler, G. and Milstein, C., "Continuous Cultures of Fused Cells Secreting Antibody of Predefined Specificity," Nature, Aug. 7, 1975, vol. 256, pp. 495-497.
Hong, Young-Kwon et al., "Prox1 is a Master Control Gene in the Program Specifying Lymphatic Endothelial Cell Fate," Developmenal Dynamics, 2002, vol. 225, pp. 351-357.
Hassan, Bassem et al., "Prospero is a Panneural Transcription Factor that Modulates Homeodomain Protein Activity," Proc. Natl. Acad. Sci. USA, Sep. 1997, vol. 94, pp. 10991-10996.
Dyer, Michael A. et al, "Prox1 Function Controls Progenitor Cell Proliferation and Horizontal Cell Genesis in the Mammalian Retna," Nature Genetics, May 2003, vol. 34, pp. 53-58.
Dudas, J. et al., "The Homeobox Transcription Factor Prox1 is Highly Conserved in Embryonic Hepatoblasts and in Adult and Transformed Hepatocytes, But is Absent from Bile Duct Epithelium," Anat. Embryol, 2004, vol. 208, pp. 359-366.
De Coupade, Catherine et al., "Novel Human-Derived Cell-Penetrating Peptides for Specific Subcellular Delivery of Therapeutic Biomolecules," Biochem. Journal, 2005, vol. 390, pp. 407-418.
Cui, Wenwu et al., "Mafs, Prox1, and Pax6 Can Regulate Chicken βB1-Crystallin Gene Expression," Journal of Biological Chemistry, Mar. 2004, vol. 279, No. 12, pp. 11088-11095.
Cook, Tiffany et al., "Distinction Between Color Photoreceptor Cell Fates is Controlled by Prospero in Drosphila," Developmental Cell, Jun. 2003, vol. 4, pp. 853-864.
Chen, Xiaoren et al., "Production of Monoclonal Antibodies Against Prox1," Hybridoma, 2006, vol. 25, No. 1, pp. 27-33.
Burke, Zoe and Oliver, Guillermo, "Prox1 is an Early Specific Marker for Developing Liver and Pancreas in the Mammalian Forgut Endoderm," Mechanisms of Development, 2002, vol. 118, pp. 147-155.
Burglin, T.R., "A *Caenorhabditis elegans* Prospero Homologue Defines a novel Domain," Trends in Biochem. Science, Feb. 1994, vol. 19, pp. 70-71.
Bi, Xiaolin et al., "The Carboxy Terminus of Prospero Regulates Its Subcellular Localization," Molecular and Cellular Biology, Feb. 2003, vol. 23, No. 3, pp. 1014-1024.
Sosa-Pineda, Beatriz et al., "Hepatocyte Migration During Liver Development Requires Prox1," Nature Genetics, Jul. 2000, vol. 25, pp. 254-255.
Ryter, Jodi M. et al., "Structure of the DNA Binding Region of Prospero Reveals a Novel Homeo-Prospero Domain," Structure, Nov. 2002, vol. 10, pp. 1541-1549.
Reis-Filho, Jorge Sergio and Schmitt, Fernando C., "Lymphangiogenesis in Tumors: What Do We Know?" Microscopy Research and Technique, 2003, vol. 60, pp. 171-180.
Reed, Nathan A. et al, "An Immunohistochemical Method for the Detection of Proteins in the Vertebrate Lens," Journal of Immunological Methods, 2001, vol. 253, pp. 243-252.
Qin, Jun et al., "Prospero-Related Homeobox (Prox1) is a Corepressor of Human Liver Receptor Homolog-1 and Suppresses the Transcription of the Cholesterol 7-α-Hydroxylase Gene," Molecular Endocrinology, 2004, vol. 18, No. 10, pp. 2424-2439.
Petrova, Tatiana V. et al., "Lymphatic Endothelial Reprogramming of Vascular Endothelial Cells by the Prox-1 Homeobox Transcription Factor," The EMBO Journal, 2002, vol. 21, No. 17, pp. 4593-4599.
Oliver, Guillermo et al., "Prox 1, a Prospero-Related Homeobox Gene Expressed During Mouse Development," Mechanisms of Development, 1993, vol. 44, pp. 3-16.
Nelson, P.N. et al., "Monoclonal Antibodies," J. Clinical. Pathol: Mol. Path, 2000, vol. 53, pp. 111-117.
Lengler, Johannes et al., "Antagonistic Action of Six3 and Prox1 at the γ-Crystallin Promoter," Nucleic Acids Research, 2001, vol. 29, No. 2, pp. 515-526.

(Continued)

*Primary Examiner*—Phillip Gambel
*Assistant Examiner*—Sharon Wen
(74) *Attorney, Agent, or Firm*—RatnerPrestia

(57) ABSTRACT

Monoclonal antibodies to Prox1 of vertebrates (pfam05044.5; NM_002763.3) and two continuous cell lines for their production are disclosed. These antibodies are particularly useful in immunoassays to detect the presence of Prox1 protein in vertebrate tissues and cells.

13 Claims, 3 Drawing Sheets

OTHER PUBLICATIONS

Van Der Auwera, Ilse et al., "Increased Angiogenesis and Lymphangiogenesis in Inflammatory Versus Noninflammatory Breast Cancer by Real-Time Reverse Transcriptase-PCR Gene Expression Quantification," Clinical Cancer Research, Dec. 2004, vol. 10, pp. 7965-7971.

Tomarev, Stanislav I et al., "Characterization of the Mouse Prox1 Gene," Biochemical and Biophysical Research Communications, 1998, vol. 248, pp. 684-689.

Tomarev, Stanislav I et al., "Chicken Homeobox Gene Prox 1 Related to Drosophila Prospero is Expressed in the Developing Lens and Retina," Developmental Dynamics, 1996, vol. 206, pp. 354-367.

Chatenoud, Lucienne, "Monoclonal Antibody-Based Strategies in Autoimmunity and Transplantation," Methods in Molecular Medicine, 2005, vol. 109, pp. 297-328.

Doe, Chris Q. et al., "The Prospero Gene Specifies Cell Fates in the Drosophila Central Nervous Systems," Cell, May 1991, vol. 65, pp. 451-464.

Al-Rawi, M.A.A. et al., "Lymphangiogenesis and Its Role in Cancer," Histology and Histophathology, 2005, vol. 20, No. 1, pp. 283-298.

Kellogg, Douglas R. and Moazed, Danesh, "Protein- and Immunoaffinity Purification of Multiprotein Complexes," Methods in Enzymol, 2002, vol. 351, pp. 172-183.

Zinovieva, Rina D. et al., "Structure and Chromosomal Localization of the Human Homeobox Gene Prox 1," Genomics, 1996, vol. 35, pp. 517-522.

Yousef, Mmohammad S. and Matthews, Brian W., "Structural Basis of Prospero-DNA Interaction: Implications for Transcription Regulation in Developing Cells," Structure, Apr. 2005, vol. 13, pp. 601-607.

Yoo, Ester M. et al., "Myeloma Expression Systems," Journal of Immunological Methods, 2002, vol. 261, pp. 1-20.

Wilting, Jorg et al., "The transcription factor Prox1 is a marker for lymphatic endothelial cells in normal and diseased human tissues," The FASEB Journal, 2002, vol. 16, pp. 1271-1273.

Wigle, Jeffrey T. et al., "An essential role for Prox1 in the induction of the lymphatic endothelial cell phenotype," The EMBO Journal, 2002, vol. 21, No. 7, pp. 1505-1513.

Wigle, Jeffrey T. and Oliver, Guillermo, "Prox 1 function is required for the development of the murine lymphatic system," Cell, Sep. 1999, vol. 98, pp. 769-778.

HYBRIDOMA CELL LINES AND MONOCLONAL ANTIBODIES RECOGNIZING PROX1

REFERENCE TO RELATED APPLICATIONS

This application claims the benefit of U.S. Provisional Application No. 60/710,921 filed Aug. 24, 2005, which is incorporated herein by reference in its entirety.

REFERENCE TO U.S. GOVERNMENT SUPPORT

The present invention was supported in part by a grant from the National Institutes of Health, National Eye Institute (Grant No. RO1EY012221). The United States Government has certain rights in the invention.

FIELD OF THE INVENTION

The invention is directed to monoclonal antibodies against vertebrate Prox1 (pfam05044.5), hybridomas producing said antibodies, and uses of the hybridomas and antibodies for the immunodetection of Prox1 in diverse vertebrates from humans to reptiles, as well as for diagnostics and treatment. These exemplary cell lines were deposited with the American Type Culture Collection (ATCC), Manassas, Va., on Jul. 12, 2005 and assigned ATCC Patent Deposit No. PTA-6854 for cell-line 4G10 and ATCC Patent Deposit No. PTA-6828 for cell-line 5G10. This deposit will be maintained under the terms of the Budapest Treaty on the International Recognition of the Deposit of Microorganisms for the Purposes of a Patent Procedure.

BACKGROUND OF THE INVENTION

In 1975, it was reported that individual, normal antibody-secreting cells could be fused with myeloma cells to produce continuous cell lines which stably secreted monoclonal antibodies (G. Kohler et al. (1975) "Continuous cultures of fused cells secreting antibody of predefined specificity", Nature 256: 495-497). Since then, numerous publications and patents have described the production and use of monoclonal antibodies to diverse antigens. See the following reviews for more details. (E. M. Yoo et al. (2002) "Myeloma expression systems", Journal of Immunological Methods 261: 1-20; P. N. Nelson et al. (2000) "Monoclonal Antibodies", Molecular Pathology 53: 111-117).

In monoclonal antibody production, each hybridoma cell synthesizes a homogeneous or monoclonal immunoglobulin population that represents one of many antibodies which are produced by the spleen of the immunized animals used to create the hybridoma cell. For example, U.S. Pat. No. 5,055, 405 discloses the production of hybridoma cell lines which produce antibodies against the periodontal pathogen, *Treponema denticola*. And U.S. Pat. No. 6,818,215 discloses the production of hybridoma cell lines which produce antibodies against senescent cell-derived inhibitors of DNA synthesis. The present invention discloses antibodies specific to Prox1 from diverse vertebrate species.

Mouse Prox1 was first identified in 1993 as a vertebrate gene related to the *Drosophila* protein Prospero (G. Oliver, et al. (1993) "Prox1, a Prospero-related homeobox gene expressed during murine development", Mechanisms of Development 44: 3-16). Subsequently, Prox1 genes were found in diverse vertebrates including chicken, human and newts. Deletion of the Prox1 gene from the mouse genome showed that it was essential for development of the eye, liver, and lymphatic system (J. T. Wigle et al. (1999) "Prox1 function is crucial for mouse lens-fiber elongation", Nat. Genet. 21: 318-322). Rabbit polyclonal antibodies specific to human Prox1 were developed and used to detect this protein in the developing eye (M. K. Duncan et al. (2002) "Prox1 is differentially localized during lens development", Mech. Dev. 112: 195-198). Subsequently, Prox1 was shown to be an excellent marker to differentiate lymphatic vessels from blood vessels in vivo (Y. K. Hong et al. (2002) "Prox1 is a master control gene in the program specifying lymphatic endothelial cell fate", Dev. Dyn. 225: 351-357). Since many cancers metastasize to lymph nodes, some investigators have reported the presence of lymphatic vessels as predictive of the ability of a tumor to metastasize.

Prox1 is the vertebrate homolog of Prospero, a divergent homeodomain protein important for neuroblast fate determination and photoreceptor development in *Drosophila* (C. Q. Doe et al. (1991) "The Prospero gene specifies cell fates in the *Drosophila* central nervous system", Cell 65: 451-464; B. Hassan et al. (1997) "Prospero is a panneural transcription factor that modulates homeodomain protein activity", Proc. Natl. Acad. Sci. USA 94: 10991-10996; T. Cook et al. (2003) "Distinction between color photoreceptor cell fates is controlled by Prospero in *Drosophila*", Dev. Cell 4: 853-864). Human Prox1 is a 736 amino acid protein containing an N-terminal nuclear localization signal, three nuclear receptor boxes, a nuclear export signal and a highly conserved C-terminus containing the divergent homeodomain and the novel Prospero domain (T. R. Burglin (1994) "A *Caehorhabditis elegans* homologue defines a novel domain", Trends Biochem. Sci. 19: 70-71; S. I. Tomarev et al. (1998) "Characterization of the mouse Prox1 gene", Biochem. Biophys. Res. Commun. 248: 684-689; J. Qin et al. (2004) "Prospero-related homeobox (Prox1) is a corepressor of human liver receptor homolog-1 and suppresses the transcription of the cholesterol 7-alpha-hydroxylase gene", Mol. Endocrinol. 18: 2424-2439). Prox1 is highly expressed in lens fiber cells (M. K. Duncan et al. (2002) "Prox1 is differentially localized during lens development", Mech. Dev. 112: 195-198) and Prox1 null mice are defective in lens fiber cell elongation (J. T. Wigle et al. (1999) "Prox1 function is crucial for mouse lens-fibre elongation", Nat. Genet. 21: 318-322) and the differentiation of retinal horizontal cells (M. A. Dyer et al. (2003) "Prox1 function controls progenitor cell proliferation and horizontal cell genesis in the mammalian retina", Nat. Genet. 34: 53-58). In this context, Prox1 functions as a transcription factor and has been shown to transactivate both the chicken βB1- and mouse γF-crystallin promoters (J. Lengler et al. (2001) "Antagonistic action of six3 and prox1 at the gamma-crystallin promoter", Nucleic Acids Res. 29: 515-526; W. Cui et al. (2004) "Mafs, Prox1 and Pax6 can regulate chicken beta B1-crystallin gene expression", J. Biol. Chem. 279: 11088-11095).

While Prox1 is critical for eye development, the correct dosage of this protein is essential for embryogenesis since heterozygous Prox 1 null mice die shortly after birth on most genetic backgrounds while homozygous Prox1 nulls die at 14.5 dpc (J. T. Wigle et al. (1999) "Prox1 function is crucial for mouse lens-fibre elongation", Nat. Genet. 21: 318-322; J. T. Wigle et al. (1999) "Prox1 function is required for the development of the murine lymphatic system", Cell 98: 769-778). Analysis of these animals has shown that Prox1 is essential for the delamination of hepatocytes from the liver bud into the surrounding mesenchyme which is necessary for normal liver development (B. Sosa-Pineda et al. (2000) "Hepatocyte migration during liver development requires Prox1", Nat. Genet. 25: 254-255). Expression studies have shown Prox1 to be one of the earliest molecular markers of liver/pancreatic fated ventral foregut endoderm (Z. Burke et al. (2002) "Prox1 is an early specific marker for the developing liver and pancreas in the mammalian foregut endoderm", *Mech. Dev.* 118: 147-155). Prox1 expression is maintained in hepatoblasts and hepatocytes throughout development and is highly upregulated in transformed hepatoma cell lines (J. Dudas et al. (2004) "The homeobox transcription factor Prox1 is highly conserved in embryonic hepatoblasts and in adult and transformed hepatocytes, but is absent from bile duct epithelium", *Anat. Embryol.* (Berl) 208: 359-366). Prox1 interacts with liver receptor homolog-1 (LRH-1), a transcription factor essential for the expression of enzymes important for bile acid synthesis, repressing LRH-1 transcriptional activity by impairing its binding to DNA (J. Qin et al. (2004) "Prospero-related homeobox (Prox1) is a corepressor of human liver receptor homolog-1 and suppresses the transcription of the cholesterol 7-alpha-hydroxylase gene", *Mol. Endocrinol.* 18: 2424-2439).

Prox 1 is also a key player in the formation of the lymphatic system (Y. K. Hong et al. (2002) "Prox1 is a master control gene in the program specifying lymphatic endothelial cell fate", *Dev. Dyn.* 225: 351-357). Expression of Prox1 in a subpopulation of venous endothelial cells is one of the first indications that lymphangiogenesis has been initiated and cells biased to a lymphatic phenotype (J. T. Wigle et al. (2002) "An essential role for Prox1 in the induction of the lymphatic endothelial cell phenotype", *Embo. J* 21: 1505-1513). Prox1 null mice do not develop lymphatics due to arrested endothelial budding from the primary vascular network (J. T. Wigle et al. (1999) "Prox1 function is required for the development of the murine lymphatic system", *Cell* 98: 769-778). Overexpression of Prox1 can reprogram blood vascular endothelial cells into lymphatic endothelial cells confirming the central role of Prox1 in lymphatic specification (T. V. Petrova et al. (2002) "Lymphatic endothelial reprogramming of vascular endothelial cells by the Prox-1 homeobox transcription factor", *Embo J.* 21: 4593-4599). Immunostaining of lymphatic tissues from healthy human adults and lymphedema patients with Prox1 polyclonal antibodies showed that Prox1 is a reliable and highly specific marker for lymphatic endothelial cells in normal and pathologic human tissues (J. Wilting et al. (2002) "The transcription factor Prox1 is a marker for lymphatic endothelial cells in normal and diseased human tissues", *Faseb J.* 16: 1271-1273; J. S. Reis-Filho et al. (2003) "Lymphangiogenesis in tumors: what do we know?", *Microsc. Res. Tech.* 60: 171-180; I. Van der Auwera et al. (2004) "Increased angiogenesis and lymphangiogenesis in inflammatory versus noninflammatory breast cancer by real-time reverse transcriptase-PCR gene expression quantification", *Clin. Cancer Res.* 10: 7965-7971; M. A. Al-Rawi et al. (2005) "Lymphangiogenesis and its role in cancer", *Histol. Histopathol.* 20: 283-298). However, the routine use of Prox1 staining in the clinic to identify lymphatics in biopsy specimens is impeded by the lack of highly standardized and reproducible anti-Prox1 monoclonal antibodies. In accordance with the invention, anti-Prox1 monoclonal antibodies are provided that can be used for Prox1 immunodetection in diverse vertebrates from humans to reptiles.

SUMMARY OF THE INVENTION

The present invention concerns monoclonal antibodies that permit the quantitative and qualitative detection of Prox1 protein and production of the antibodies. The present invention provides a hybridoma cell line selected from the group consisting of 5G10 (ATCC patent deposit number PTA-6828) and 4G10 (ATCC patent deposit number PTA-6854) and monoclonal antibodies produced by the hybridomas.

Another aspect of the invention provides a conjugate comprising an antibody produced by hybridoma cell line 5G10 or 4G10 conjugated directly or indirectly to a detectable label.

A further aspect of the invention provides a method of producing an antibody comprising the step of culturing cells of the hybridoma cell line 5G10 or 4G10 under conditions that permit production of the antibody.

An additional aspect of the invention provides a method for detection of Prox1 in a sample comprising the steps of contacting sample suspected of containing Prox1 with the antibody produced by hybridoma cell line 5G10 or 4G10; and detecting binding of the antibody with Prox1, thereby signaling the presence of Prox1 in the sample. Preferably, the sample is a sample of mammalian tissue.

The invention additionally provides a kit for detection of Prox1 comprising: (i) a monoclonal antibody of claim 4; (ii) a means of support, on which is attached the monoclonal antibody; (iii) a washing solution; and (iv) a means for signal generation.

The invention further provides a method of modulating Prox1 function in a cell or a mammal comprising administering to the cell or mammal the monoclonal antibody produced by hybridoma 4G10 or 5G10 conjugated to a cell permeant molecule in an amount sufficient to modulate Prox1 function.

These and other aspects of the invention are set out in the appended claims and described in the following Detailed Description.

BRIEF DESCRIPTION OF THE DRAWINGS

In FIG. 2, T refers to transfected 293T cell extracts; N refers to un-transfected 293T cell extracts; NE refers to HepG2 cell nuclear extracts and TE refers to HepG2 cell total extracts.

DETAILED DESCRIPTION OF THE INVENTION

Figure 1:
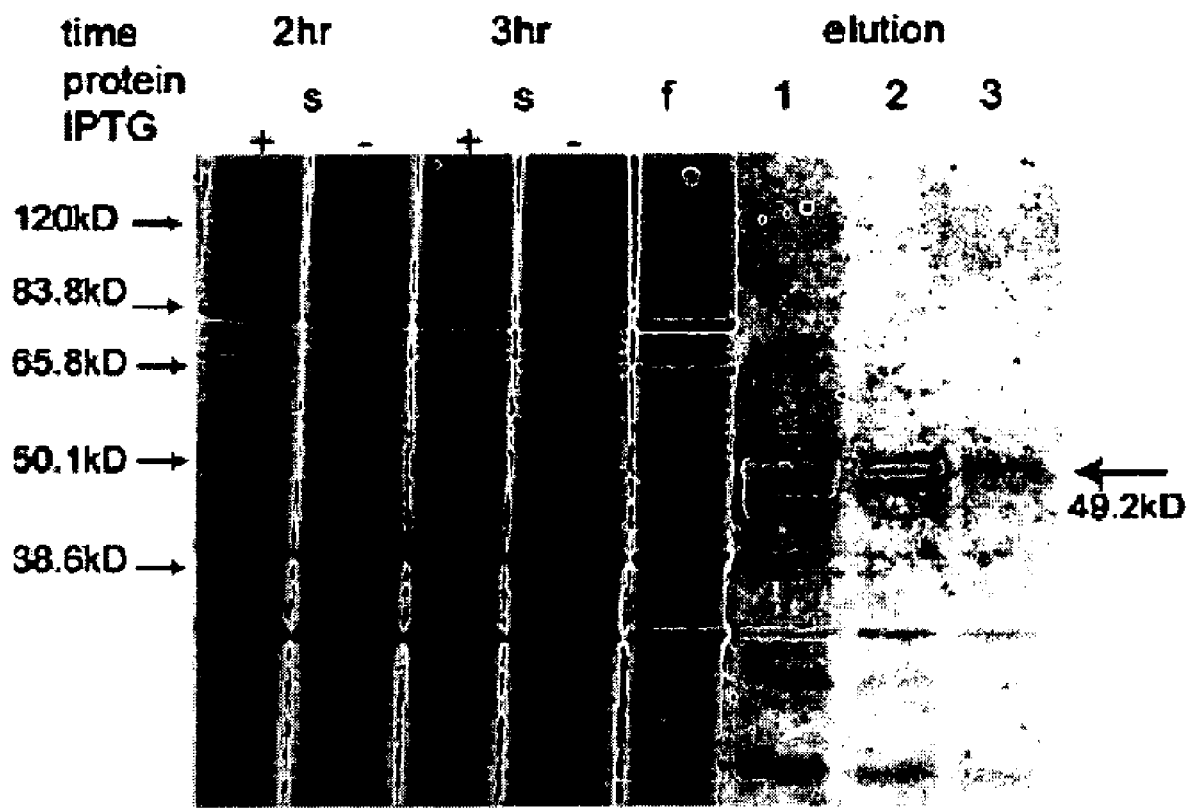
FIG. 1—Induction and purification of recombinant human Prox1-GST in BL21(DE3) CodonPlus®-RIL *E.coli* assayed by SDS-PAGE. No recombinant protein was observed without induction, while recombinant protein was obtained in the soluble fraction 2 hours after the addition of IPTG. (s, protein from the soluble fraction; +, with IPTG; −, without IPTG). Recombinant Prox1 was captured froma 500 ml culture two hours after IPTG induction with glutathione beads and eluted with three independent elution buffer treatments. The recombinant protein with an expected molecular weight 49.2 kDa is predominantly found in the first two elution buffer treatments. (f, flow through after glutathione bead incubation).

The present invention concerns monoclonal antibodies that permit the quantitative and qualitative detection of Prox1 protein and their production. Two hybridoma cell lines capable of producing IgG to Prox1 were formed by fusing a-non-secreting mouse myeloma cells with spleen cells from a mouse immunized with a recombinant fusion protein generated between glutathione S-transferase and amino acids 547-737 of Prox1 of human origin. Thus, this invention comprises the hybridoma cell lines formed and the monoclonal antibodies produced from these hybridomas.

Presently, monoclonal antibodies are used routinely in the pathology laboratory to detect the presence or absence of proteins diagnostic for disease or predictive of the clinical outcome of cancer. They are advantageous over polyclonal antibodies since they can be produced in unlimited amounts, each lot having identical specificity and affinity. This makes monoclonal antibodies especially advantageous reagents to detect protein expression in the human clinical setting. For this reason, the monoclonal antibodies recognizing Prox1 are particularly useful for the detection of Prox1 in human tissue, particularly to monitor lymphatic spread of human cancers. Further, the ability of the monoclonal antibodies to recognize Prox1 in diverse vertebrates makes them useful to study the development of Prox1 expressing tissues.

Moreover, due to the specific reactivity of the antibodies, the monoclonal antibodies of the invention are useful for the detection of Prox1 in the presence of other proteins usually found in tissues. Due to the known distribution of Prox1 in tissue, these antibodies are useful in diagnostic applications to detect the presence of lymphatic vessels and lymphatic endothelial cells in tissue, to detect Prox1 expressing cells in diverse vertebrates, and to diagnose Prox1-related conditions in a vertebrate. Since the presence of lymphatic vessels in cancer may correlate with the cancer's metastatic potential, the monoclonal antibodies of the invention can also be used to identify lymphatic vessels in biopsy tissue and assist in deciding the aggressiveness of a patient's treatment.

The recombinant human Prox1 protein used to make the antibodies of this invention consist of amino acids 547 to 737 fused to an N-terminal GST tag. This region of Prox1 contains the atypical homeodomain which consists of three α-helices and an N-terminal extension held together by hydrophobic interactions as well as the Prospero domain which folds into four α-helices. These two domains fold together into an integrated structural unit that restricts the DNA binding potential of Prox1 to the N-terminal amino acids of the last α-helix of the homeodomain (J. M. Ryter et al. (2002) "Structure of the DNA binding region of Prospero reveals a novel homeo-Prospero domain", *Structure (Camb)* 10: 1541-1549; M. S. Yousef et al. (2005) "Structural basis of Prospero-DNA interaction: implications for transcription regulation in developing cells", *Structure (Camb)* 13: 601-607). The Prospero domain also masks the nuclear export signal (NES) located at the very beginning of the homeodomain (X. Bi et al. (2003) "The carboxy terminus of Prospero regulates its subcellular localization", *Mol. Cell Biol.* 23: 1014-1024), likely contributing to the dual localization of Prox1 in both cytoplasm and nucleus (M. K. Duncan et al. (2002) "Prox1 is differentially localized during lens development", *Mech. Dev.* 112: 195-198). The recombinant protein is likely to retain at least some of its native conformation since it is able to bind to Prox1 sites found in the chicken βB1-crystallin promoter in electrophoretic mobility shift assays (W. Cui et al. (2004) "Mafs, Prox1 and Pax6 can regulate chicken beta B1-crystallin gene expression", *J. Biol. Chem.* 279: 11088-11095).

The recombinant protein was then used to create hybridomas capable of immunofluorescent detection of Prox1 in tissue sections derived from humans, rats, chickens and lizards. The portion of Prox1 used to produce these hybridomas is highly conserved, with only two conservative amino acid differences detected between humans and mice, while only one conservative amino acid difference is seen between the human and chicken proteins (S. I. Tomarev et al. (1966) "Chicken homeobox gene Prox1 related to Drosophila Prospero is expressed in the developing lens and retina," *Dev. Dynam.* 206: 354-367; R. D. Zinovieva et al. (1966) "Structure and chromosomal localization of the human homeobox gene Prox1," *Genomics* 35: 517-522; S. I. Tomarev et al. (1998) "Characterization of the mouse Prox 1 gene," *Biochem. Biophys. Res. Commun.* 248: 684-689).

The invention provides for two monoclonal antibodies of different isotypes against the highly conserved human Prox1 homeo and Prospero domain. Both antibodies detected Prox1 by immunolocalization in lenses from all land vertebrates tested, from humans to lizards Further, they can detect both endogenous Prox1 and eukaryotic vector-driven Prox1 expression in cell and tissue extracts by western blot, demonstrating that they are robust reagents with diverse potential applications in the study of Prox1 function in tissue development and disease.

One embodiment of the invention is the hybridoma cell-line 5G10 that produces an IgG1 with a kappa light chain specific for Prox1 (pfam05044.5; NM_002763.3), wherein the cell line is formed by fusing a non-secreting mouse myeloma cells with a spleen cell from a mouse immunized with fusion protein formed between glutathione-5-transferase and amino acids 547-737 of Prox1 of human origin comprising the homeodomain and Prospero domain. Hybridoma cell line 5G10, which produces monoclonal antibody 5G10, was deposited in the American Type Culture Collection, Manassas, Va., USA on Jul. 12, 2005 as Patent Deposit number PTA-6828 under the terms of the Budapest Treaty.

Another embodiment of this invention is the hybridoma cell-line 4G10 that produces an IgG2b with a kappa light chain specific for Prox1 (pfam05044.5; NM_002763.3), wherein the cell line is formed by fusing a non-secreting mouse myeloma cell with a spleen cell from a mouse immunized with a fusion protein formed between glutathione-S-transferase and amino acids 547-737 of Prox1 of human origin comprising the homeodomain and Prospero domain. Hybridoma cell line 4G10, which produces monoclonal antibody 4G10, was deposited in the American Type Culture Collection, Manassas, Va., USA on Jul. 12, 2005 as Patent Deposit No. PTA-6854 under the terms of the Budapest Treaty.

In one embodiment, the strain of the immunized mouse is BALB/c. In another embodiment the myeloma cell is P3.

A further embodiment of the invention is a cell of the hybridoma cell line 4G10 or 5G10.

Another embodiment of the invention provides monoclonal antibody 5G10 specific for Prox1 (pfam05044.5; NM_002763.3), said antibody produced by fusing a non-secreting mouse myeloma cell with a spleen cell from a mouse immunized with a fusion protein formed between glutathione-S-transferase and amino acids 547-737 of Prox1 of human origin comprising the homeodomain and Prospero domain. Monoclonal antibody 5G10 is produced by hybridoma cell line 5G10. This monoclonal antibody has specificity for vertebrate Prox1 as determined by enzyme-linked immunoassay, western blotting and immunolocalization.

An additional embodiment of the invention provides monoclonal antibody 4G10 specific for Prox1 (pfam05044.5;

NM_002763.3), said antibody produced by fusing a non-secreting mouse myeloma cell with a spleen cell from a mouse immunized with a fusion protein formed between glutathione-S-transferase and amino acids 547-737 of Prox1 of human origin comprising the homeodomain and Prospero domain. Monoclonal antibody 4G10 is produced by hybridoma cell line 4G10 discussed above. This monoclonal antibody has specificity for vertebrate Prox1 as determined by enzyme-linked immunoassay, western blotting and immunolocalization.

The invention provides a method of making an antibody comprising the step of cultivating cells of hybridoma lines 4G10 and 5G10 under conditions that permit production of the antibody. Typically, antibodies can be produced by culturing the hybridoma cells in mice according to procedures known in the art.

In a further embodiment, the invention comprises monoclonal antibodies specific to Prox1. The antibodies of the invention can be mouse, human, humanized, and/or chimeric (L. Chatenoud (2005) "Monoclonal antibody-based strategies in autoimmunity and transplantation", *Methods Mol Med*. 109: 297-328).

The monoclonal antibodies can be purified or isolated using standard procedures known in the art.

The invention also encompasses the use of the monoclonal antibodies in assay methods and kits. An immunoassay kit for the detection of Prox 1 can be used for detection of Prox1 in tissues from vertebrates. For example, the kit may comprise: (i) a monoclonal antibody specific to Prox1 produced by hybridoma cell-lines 4G10 deposited under ATCC Patent Deposit No. PTA-6854; or a monoclonal antibody specific to Prox1 produced by hybridoma cell-lines 5G10 deposited under ATCC Patent Deposit No. PTA-6828; (ii) a means of support, on which is attached said monoclonal antibody specific to Prox1 produced by hybridoma 4G10 or 5G10; (iii) a washing solution; and (iv) a means for signal generation. A kit may comprise a vessel or vessels containing the monoclonal antibodies of the invention.

Another aspect of the present invention provides a conjugate comprising an antibody of the present invention conjugated directly or indirectly to a detectable label. The antibody can be conjugated directly to the detectable label so that a covalent link exists between the label and the antibody, or indirectly such as through a biotin-avidin linkage or another antibody. Detectable labels for use in immunoassays and methods for detecting the labels are well known in the art. Suitable detectable labels include, but are not limited to an enzyme label, a radiolabel, a fluorescent label, a chemiluminescent label, a bioluminescent label, or a particulate label. Enzyme labels include horseradish peroxidase, β-galactosidase, and alkaline phosphatase. Radiolabels include $^{32}P$, $^{3}H$, $^{14}C$, $^{35}S$, $^{125}I$, or $^{131}I$. Detection of the label can be by methods such as scintillation counting, gamma ray spectrometry or autoradiography. Bioluminescent labels, such as derivatives of firefly luciferin, are also useful. Fluorogens may also be used to label proteins. Suitable fluorescent labels include fluorescein and derivatives, phycoerythrin, allo-phycocyanin, phycocyanin, rhodamine, and Texas Red. The fluorogens are generally detected by a fluorescence detector. Among the particulate labels that can be used are latex labels and colloidal metal labels such as colloidal gold, silver, tin, and other metals.

In an alternative embodiment, the monoclonal antibodies can be used in assay methods. Since the presence of lymphatic vessels in cancer may correlate with the cancer's metastatic potential, the monoclonal antibodies of the invention can be used to identify lymphatic vessels in biopsy tissue and assist in deciding the aggressiveness of a patient's treatment. For example, thin sections would be made of a tissue biopsy or excised tumor, the monoclonal antibody specific to Prox1 produced by hybridoma 4G10 or 5G10 would be applied to the tissue, incubated, washed, and then detected with a labeled anti-mouse IgG. Alternatively, thin sections would be made of a tissue biopsy or excised tumor, the monoclonal antibody specific to Prox1 produced by hybridoma 4G10 or 5G10 directly labeled, would be applied to the sections, washed and the signal produced by the label detected.

The invention also encompasses therapeutic and research uses of the monoclonal antibodies specific to Prox1. For example, these antibodies could be conjugated to a cell permeant molecule and transferred into cells, tissues, animals or humans for research and/or therapies designed to modulate Prox1 function. (C. de Coupade, et al. (2005) "Novel human derived cell penetrating peptides for specific subcellular delivery of therapeutic biomolecules'" *Biochem J.* Apr. 29, 2005).

In a further embodiment, the invention comprises the use of the monoclonal antibodies specific to Prox1 for immunoaffinity protein purification (D. R. Kellogg, et al. (2002) "Protein- and immunoaffinity purification of multiprotein complexes", *Methods Enzymol*. 351: 172-83). For example, Prox1 protein can be purified from a biological sample containing Prox1 by a method using an affinity matrix comprising monoclonal antibody produced by hybridoma 4G10 or 5G10 bound to a solid support; contacting the biological sample with the affinity matrix, to produce an affinity matrix-Prox1 complex; separating the affinity matrix-Prox1 complex from the remainder of the biological sample; and releasing Prox1 from the affinity matrix.

All the references described herein are incorporated by reference in their entirety.

The invention is illustrated by the following examples which are not to be construed as limiting.

Hybridoma cell line 4G10, which produces monoclonal antibody 4G10, was deposited in the American Type Culture Collection, Manassas, Va., USA on Jul. 12, 2005 as Patent Deposit number PTA-6854 under the terms of the Budapest Treaty. Hybridoma cell line 5G10, which produces monoclonal antibody 5G10, was deposited in the American Type Culture Collection, Manassas, Va., USA on Jul. 12, 2005 as Patent Deposit number PTA-6828 under the terms of the Budapest Treaty.

EXPERIMENTAL

Materials and Methods

Production and Purification of the Recombinant Prox1-GST Fusion Protein

A partial cDNA encoding the homeo- and Prospero domain of human Prox1 (R. D. Zinovieva et al. (1966) "Structure and chromosomal localization of the human homeobox gene Prox1," Genomics 35: 517-522) was ligated into the BamHI and EcoRI site of the pET-41a(+) vector (Novagen, Madison, Wis.) to produce a recombinant gene consisting of an in-frame fusion between Prox1 (aa 547 to 737) and a glutathione S-transferase (GST) tag. The vector was transformed into BL-21 (DE3) CodonPlus®-RIL *Escherichia coli* (Stratagene, La Jolla, Calif.) and protein production was initiated by growing a 500 ml culture of LB broth overnight at 35° C. After the optical density of the 500 ml culture reached 0.6 (OD 600 nm), induction was initiated with a final concentration of 1 mM IPTG and cells were harvested after two hours of induction.

The cells were lysed using BUGBUSTER® Protein Extraction Reagent (Novagen, Calif.) and the soluble and insoluble fractions separated by centrifugation. The soluble fraction mixed with GST-BIND™ resin (Novagen) to capture the GST-Prox1 fusion protein, the beads washed and the recombinant protein eluted with glutathione according to the manufactruer's protocol (Novagen). The purity of the protein was analyzed by SDS-PAGE.

Immunization

BALB/c mice were immunized with 50 µg of Prox1-GST fusion protein in 200 µl of RIBI adjuvant (Corixa, Hamilton, Mont.). The animals were injected subcutaneously at two sites with 0.1 ml for each site and boosted 3 weeks and 15 weeks after the first injection. A final tail vein injection of 100 µg of Prox1-GST in 0.1 ml of saline was given 11 days after the final boost to more effectively stimulate the spleen.

The Fusion

Three days after the final intravenous injection of GST-Prox 1, mice were bled retroorbitally to determine the titer of the antibodies being produced and $5 \times 10^7$ spleen cells were fused with the same number of P3X63Ag8.653 myeloma cells in the presence of 50% polyethylene glycol (PEG). Selection of hybridomas was accomplished using HAT media (IMDM, 10 mM sodium hypoxthanine, 1.6 mM thymidine, 40 µM aminopterin).

Screening of Hybridomas by ELISA

In order to determine the specificities of each hybridoma cell line, 96-well microtiter plates were coated with 100 µl of a 5 µg/ml solution of either Prox1-GST or GST alone in coating buffer (14.2 mM $Na_2CO_3$, 34.9 mM $NaHCO_3$, 3.1 mM $NaN_3$), and incubated overnight at 4° C. The plates were washed with PBS-Tween, (10 mM sodium phosphate, 0.9% saline, Tween-20, pH 7.4) and incubated overnight with 100 µl of a 1:2 dilution of hybridoma supernatant in PBS-Tween. The plates were again washed three times with PBS-Tween and incubated for 1 hour with 100 µl of a 1:10,000 dilution of a rabbit anti-mouse IgG alkaline phosphatase conjugate (Sigma, St. Louis, Mo.) at room temperature. The plate was washed again as before with PBS-Tween and developed by adding 100 µl of a 2 mg/ml solution of Sigma 104 phosphatase substrate in substrate buffer to each well. The plate was incubated at 37° C. for 10 minutes and was read at 410 nm on a MRX Revelation plate reader (Dynex Technologies, Chantilly, Va.). Those clones that gave the highest positive ELISA readings for Prox 1-GST but low readings for GST alone were chosen for further analysis.

Limiting Dilution and Subcloning

Positive cell lines were plated at both 5 cells/well and 1 cell/well in 48 wells of a 96 well plate and cultured in IMDM with 10% FBS under standard conditions. The media of wells with growing cells was screened by ELISA and wells with single colonies and the highest ELISA readings were chosen for further analysis. Subcloning of positive cell lines by limiting dilution was repeated until all wells with growing cells had positive ELISA signals. The specific immunoglobulin subclass that each hybridoma secreted was determined using the ImmunoPure Monoclonal Antibody Isotyping Kit II (AP/PNPP) (Pierce, Ill.). The positive clones were frozen down in 0.5 ml of freezing media (fetal bovine serum with 10% DMSO) and stored in liquid nitrogen.

Preparation of High Concentration Anti-Prox1 Antibodies

The hybridoma cell lines were thawed and cultured in IMDM with 10% FBS under standard conditions. BALB/c mice were primed with an intraperitoneal injection of 0.5 ml of Pristane (Sigma, Mo.). One week after priming, cultured hybridoma cells were harvested and diluted in PBS to a concentration of $3 \times 10^6$ cells per ml. One ml of cells was injected intraperitoneally into each mouse. Mice were monitored daily for abdominal distention and ascites tapped by standard methods. The collected ascites were centrifuged and the supernatants were collected and stored at −80° C. with added EDTA and $NaN_3$ to final concentrations of 0.02%.

Preparation of Full Length Prox1

The pCMV-Prox1 vector has been previously described (Cui et al. (2004) "Mafs, Prox1 and Pax6 cooperate to direct βB1-crystallin gene expression, "*Journal of Biological Chemistry* 279: 11088-1095). The fibroblast cell line 293T (provided by Dr. Robert Sikes, University of Delaware) was grown in DMEM (Invitrogen, Calif.) supplemented with 10% fetal bovine serum (Invitrogen) at 37° C. and 5% $CO_2$. Cells were then plated onto 100 mm dishes at a density of $6 \times 10^6$/plate and transfected at 50% confluence with the expression constructions using LIPOFECTAMINE™ transfection reagent (Invitrogen). Each plate was transfected with 16 µg of the expression plasmids pCMV-Prox1, while untransfected 293T cells were used as a negative control. Cells were harvested and lysed in RIPA lysis buffer (50mM Tris-HCl, pH 7.4, 150 mM NaCl, 0.25% deoxycholic acid, 1% NP-40, 1 mM EDTA) with added protease inhibitor cocktail (Pierce). Thirty micrograms of the cell extract were loaded for SDS-PAGE and immunoblotted with 4G10 and 5G10 ascites as described below.

SDS-PAGE and Western Blot Analysis

Chicken embryo lenses were dissected from fourteen-day embryos and homogenized in RIPA lysis buffer with added protease inhibitor cocktail. Two hundred micrograms of protein diluted 1:1 with 2× sample buffer (Bio-rad, with added 5% 2-Mercaptoethanol) was electrophoresed on an 8% SDS-PAGE gel. The protein was transferred to nitrocellulose membrane (Invitrogen) and blocked for 1 hour in super-block solution (Pierce). The membrane was then incubated with shaking overnight at 4° C. with 1:1000 diluted hybridoma ascites in the super-block solution. The membrane was washed two times with TBS-Tween and then incubated for one hour in a 1:10,000 dilution of a rabbit anti-mouse HRP enzyme conjugate (Jackson ImmunoResearch Lab, Pa.) in the super-block solution. The membrane was washed four times with TBS-Tween and then immersed in the substrate solution (Amersham) for one minute and exposed to x-ray MS film (Kodak).

The human liver-derived HepG2 cell line (American Type Cell Culture [ATCC] Manassas, Va.) was cultured in DMEM supplemented with 10% FBS at 37° C. and 5% $CO_2$. Cells were harvested and lysed in RIPA buffer to make total cell extracts. The nuclear extracts were also made using the NE-PER kit (Pierce). These extracts were subjected to SDS-PAGE and immunoblotted with 4G10 ascites as described above.

Immunofluorescent Labeling of HepG2 Cells

HepG2 cells were plated in four-well Lab-TEK II chambers (Nalge Nunc, Rochester, N.Y.) at a density of 50,000 cells per well and grown overnight. The next day, cells were washed with 1×PBS and fixed with 4% paraformaldehyde (Fisher Scientific, Hampton, N.H.) for 10 minutes. After rinsing with 1×PBS, cells were permeabilized with Triton X-100 (0.2%, Sigma) for five minutes. The cells were rinsed gently with 1×PBS twice and blocked with blocking solution (3% BSA in 1×PBS) for 30 minutes with shaking at room temperature. 5G10 ascites were then added at a 1:800 dilution (diluted in blocking solution) at room temperature for one hour. Cells were washed three times with blocking solution, 10 minutes each. Cells were then incubated with a 1:100 dilution of goat-anti mouse Alexa Fluor 488 conjugate (Molecular Probes, Eugene, Oreg.) containing a 1:2000 dilution of the nucleic acid stain DraQ5 (Biostatus, Shepshed, United Kingdom) for one hour at room temperature. Cells were washed with blocking solution three times, 10 minutes each. Finally, cells were washed once with 1×PBS, the chambers removed, and the cells mounted and viewed on a Zeiss 510 LSM confocal microscope with an Argon/Krypton laser (Zeiss, Gottingen, Germany).

Immunofluorescent Labeling of Tissue Sections

Human lenses were obtained from a 21 year old accident victim via the Oregon Lions Eye Bank. Eyes were isolated from 10 day embryonic *Gallus gallus* (chicken), 5 month old *Rattus rattus* (Sprague Dawley rat), adult *Rana pipens* (frog), adult *Anolis sagrei* (lizard) and adult *Fundulus similes* (fish). The unfixed tissue was placed in OCT (TISSUE-TEK® paraffin) and frozen on a bed of dry ice. Immunohistochemical staining was performed as previously described (Reed, et al. (2001) "An immunohistochemical method for the detection of proteins in the vertebrate lens," *Journal of Immunological Methods* 253: 243-252).) Briefly, tissue was sectioned at 16 μm and mounted on Colorfrost/Plus slides (Fisher Scientific, Pittsburgh, Pa.). The slides were fixed with ice cold 1:1 acetone:methanol for 10 minutes and blocked with 1% BSA in 1X PBS for 1 hour at room temperature. Hybridoma supernatants were diluted in 1% BSA-PBS) incubated for 1 hour at room temperature. The slides were washed twice with 1X PBS and then incubated for 1 hour at room temperature with a 1:250 dilution of goat-anti mouse Alexa Fluor® 568 conjugate (Molecular Probes, Eugene, Oreg.) in 1% BSA-PBS containing a 1:2000 dilution of the nucleic acid stain TO-PRO-3 iodide in DMSO (Molecular Probes). The slides were again washed twice with 1X PBS and theft coverslips were affixed. The slides were viewed on a Zeiss 510 LSM confocal microscope with an Argon/Krypton Laser (Zeiss, Gottingen, Germany).

Results

Antigen Production

The partial cDNA encoding amino acids 547 to 737 of human Prox1 was cloned into pET-41a(+) to form an in-frame fusion between the Prox1 and GST genes. The resulting plasmid was transformed into BL-21 CodonPlus®-RIL cells which express additional tRNAs recognizing arginine, isoleucine and leucine codons seldom used in bacteria. Protein synthesis was induced by the addition of IPTG, the soluble protein purified on GST beads and assayed for purity by SDS-PAGE (FIG. 1).

Hybridoma Production and Initial Screening of the Fusion Products

The titer of anti-Prox1-GST antibodies in the serum of the immunized mice was approximately 1:10,000 as determined by analyzing the half maximum optical density by ELISA. Immunofluorescence staining of human lens sections with this sera strongly stained the nuclei of human lens fiber cells further suggesting that the immunized mice were producing anti-Prox1 antibodies (M. K. Duncan et al. (2002) "Prox1 is differentially localized during lens development", Mech. Dev. 112: 195-198). Spleen cells from the immunized mice were fused to P3 myeloma cells and the products of this fusion were screened for the ability to produce antibodies that specifically recognize the Prox1-GST fusion protein by ELISA using plates coated with either Prox-1-GST or GST alone. The cells with the highest signals to Prox1-GST and low signals to GST by ELISA were transferred to a 24-well plate. Five cell lines survived the initial transfer and secreted antibodies capable of Prox1 immunodetection in tissue sections. Two lines, 4G10 and 5G10, were subcloned twice and both stably maintain the ability to produce anti-Prox1 antibodies. Isotyping was performed by ELISA and 4G10 was determined to produce IgG2b/κ antibodies while 5G10 produces IgG1/κ antibodies.

Large Scale Antibody Production

The 4G10 and 5G10 cell lines were injected into the abdomen of BALB/C mice for large scale antibody production. The titer of ascites from 4G10-injected mice was approximately 1:10,000 as determined by the half maximum optical density by ELISA. The titer of the 5G10-injected mice ascites was approximately 1:20,000.

Western Blotting

Figure 2:
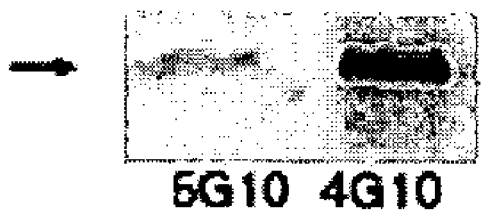
FIG. 2 shows (A) Western blots of 14d chicken embryo lens tissues, (B) transfected 293T cell extracts and (C) Hep2G cells extracts, with monoclonal antibody 4G10 and 5G10. Native Prox1 in chicken lens tissue, Hep2G cells, and cells transfected with pCMC-Prox1 vector showed a band of 83.2 kDa as indicated. Un-transfected 293T cell extracts showed no band. Both antibodies detect Prox1 in lens tissue and in transfected 293T cells, but 4G10 antibody resulted in a stronger signal.
Figure 2:
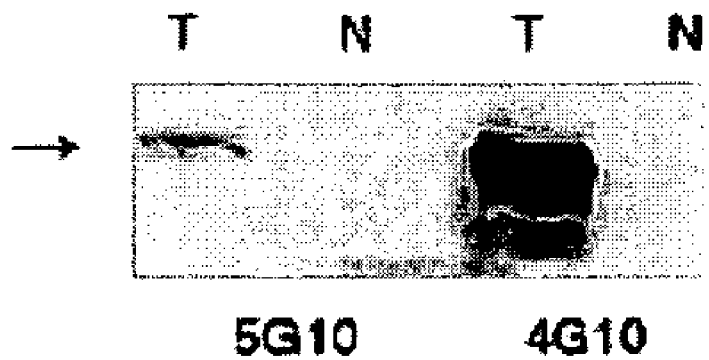
Figure 2:
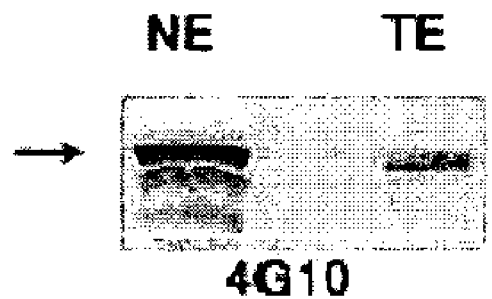

Antibodies produced by 4G10 cell line were able to easily detect Prox1 in western blots with chicken lens extracts at a 1:2000 dilution of ascites while the 5G10 cell line was only able to generate a weak band at a 1:1000 dilution (FIG. 2A). To confirm the specificity of this reaction, we transfected 293T cells with a pCMV-Prox1 eukaryotic expression vector, which produces full length human Prox1. Un-transfected 293T cells do not express Prox1 endogenously and do not produce a positive western blot signal with either antibody (FIG. 2B). In contrast, both 4G10 and 5G10 can detect the expected 83 kDa band for Prox1 in cells transfected with the Prox1 expression vector (FIG. 2*b*), showing that the antibodies are highly specific for Prox1. However, as seen for chicken Prox1, human Prox1 produces a stronger western blot signal with 4G10 than 5G10.

HepG2 cells, a transformed cells line derived from a human liver cancer, have been reported to express Prox1 mRNA. Western blotting of both HepG2 nuclear and whole cells extracts detected the expected 83-kDa band (FIG. 2C), demonstrating that 4G10 is able to detect endogenous human Prox1 as well.

Immunofluorescence in Cultured Cells

Since Hep2G cells express endogenous Prox1, detection of Prox1 was next attempted in this cell line by immunofluorescence. In Hep2G cells, antibody derived from the 5G10 hybridoma gave a robust nuclear signal in nearly all cells present in the cultures, while cells stained with secondary antibody alone gave little to no staining.

Immunofluorescence on Tissue Sections

Figure 3:
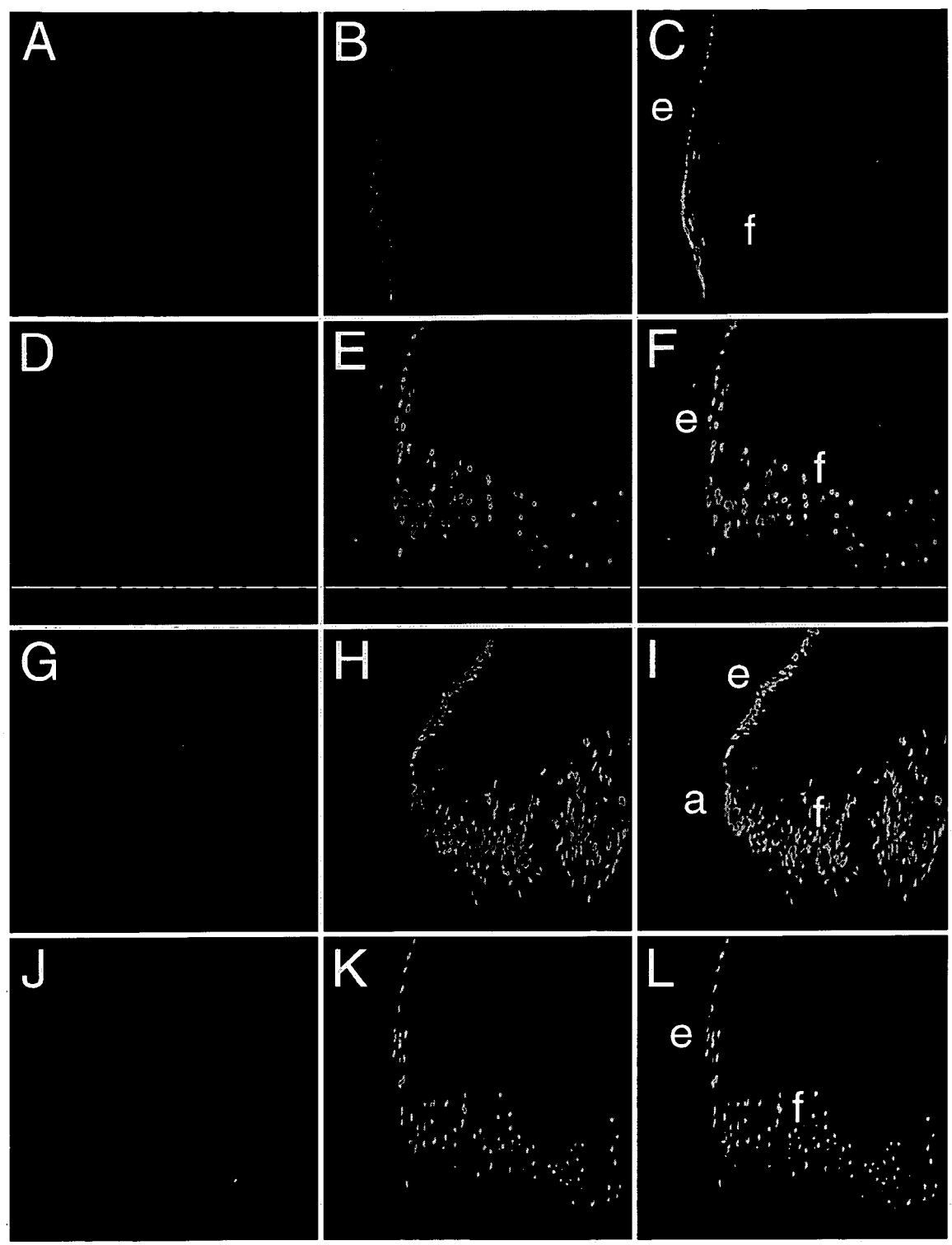
FIG. 3 shows immunofluorescence staining of lenses from various terrestrial vertebrates with the 5G10 monoclonal antibody. A-C 21-year-old human lens. D-F Five month rat lens. G-I Embryonic day ten chicken lens. J-L Adult *Anolis sagrei* (lizard) lens. a, annular pad; e, lens epithelium; f, lens fiber cells. A, D, G, J—the nuclear counterstain TO-PRO-3 in blue; B, E, H, K—Prox1 immunodetection in red; C, F, I, L—Overlap between nuclear and Prox1 immunolocalization in pink.

Ascites and purified antibodies derived from both hybridomas were used to detect Prox1 in vertebrate lenses, a tissue known to express Prox1 at appreciable levels (M. K. Duncan et al. (2002) "Prox1 is differentially localized during lens development", Mech. Dev. 112: 195-198). Hybridoma 5G10 was able to robustly detect nuclear Prox1 protein in sections derived from human, (FIG. 3*a-c*), rat (FIG. 3*d-f*), chicken (FIG. 3 *g-i*), and lizard (*Anolis sagrei*, FIG. 3 *j-l*) lenses. Frog (*Rana pipens*) lenses only stained weakly with this antibody while fish (*Fundulus similes*) lenses did not stain at all (data not shown). Hybridoma 4G10 generally produced the same pattern of results (data not shown), however, 4G10 stained tissue less intensely than 5G10 when used at the same dilution.

What is claimed is:

1. A hybridoma cell line selected from the group consisting of 5G10 (ATCC patent deposit number PTA-6828) and 4G10 (ATCC patent deposit number PTA-6854).

2. The hybridoma cell line of claim 1, wherein said cell line is 5G10 (ATCC patent deposit number PTA-6828).

3. The hybridoma cell line of claim 1, wherein said cell line is 4G10 (ATCC patent deposit number PTA-6854).

4. A monoclonal antibody produced by the hybridoma cell line of claim 1.

5. A monoclonal antibody produced by the hybridoma cell line of claim 2.

6. A monoclonal antibody produced by the hybridoma cell line of claim 3.

7. A conjugate comprising an antibody of claim 4 conjugated directly or indirectly to a detectable label.

8. A conjugate comprising an antibody of claim 5 conjugated directly or indirectly to a detectable label.

9. A conjugate comprising an antibody of claim 6 conjugated directly or indirectly to a detectable label.

10. A method of producing an antibody comprising the step of culturing cells of the hybridoma cell line of claim 1 under conditions that permit production of the antibody.

11. A kit comprising: (i) the monoclonal antibody of claim 4; (ii) a washing solution; and (iii) a detectable label.

12. The kit of claim 11 further comprising a support to which the monoclonal antibody is attached.

13. The kit of claim 11, wherein the detectable label is selected from the group consisting of an enzyme, a radiolabel, a color label, a fluorescent label, a chemiluminescent label, a bioluminescent label, and a particulate label.

* * * * *